United States Patent [19]

Berg

[11] Patent Number: 5,622,701
[45] Date of Patent: Apr. 22, 1997

[54] CROSS-REACTING MONOCLONAL ANTIBODIES SPECIFIC FOR E- AND P-SELECTIN

[75] Inventor: Ellen L. Berg, Palo Alto, Calif.

[73] Assignee: Protein Design Labs, Inc., Mountain View, Calif.

[21] Appl. No.: 259,963

[22] Filed: Jun. 14, 1994

[51] Int. Cl.$^6$ .................. A61K 39/395; C07K 16/28; C12N 5/12; C12N 15/13
[52] U.S. Cl. .................. 424/153.1; 424/152.1; 424/172.1; 424/143.1; 424/173.1; 435/70.21; 435/172.2; 435/334; 435/343; 536/23.53; 530/387.1; 530/387.3; 530/388.1; 530/388.22; 530/388.7; 530/389.6
[58] Field of Search .................. 435/240.27, 172.2, 435/69.1, 70.1, 70.21, 69.6, 172.3, 290.27; 436/548, 536; 424/133.1, 136.1, 152.1, 143.1, 172.1, 144.1, 130.1, 141.1, 1, 173.1, 184.1, 153.1; 514/885; 530/387.3, 387.1, 388.1, 380.22, 388.7, 388.73, 389.6; 536/23.53, 23.5, 23.57

[56] References Cited

U.S. PATENT DOCUMENTS 5,225,539  7/1993  Winter .................. 530/387.3

FOREIGN PATENT DOCUMENTS 07861      7/1990  WIPO .................. C12P 21/00
WO93/24614 9/1993  WIPO .................. C12N 5/18

OTHER PUBLICATIONS

Abbassi et al., "Canine neutrophil margination mediated by lectin adhesion molecule-1 in vitro," *J. Immunol.* 147:2107–2115 (1991).
Jutila et al., "Characterization of a functionally important and evolutionarily well-conserved epitope mapped to the short consensus repeats of E-selectin and L-selectin", *J. Exp. Med.* 175:1565–1573 (1992).
"Antibodies," Excerpt, R&D Systems 1993 Catalog, Minneapolis, MN.
"Adhesion Molecule Antibodies," Excerpt, R&D Systems 1994 Catalog, Minneapolis, MN.
Emery et al. Humanised mAb for Therapeutic application, Eap Opin Invest Drugs 1994 3:241–51.
Cunningham et al. Anitbody engineering—how to be human TIBTECH Apr. 1992.
Berg et al. Comparison of L-selectin & E-selectin ligand specificitiy. The L-selectin can bind The E-selectin ligands sialyl Le$^x$+ Le$^a$ Biochem & Biophys. Res. Comm. 184:1048:55 1992.
Seekamp et al. Role of selectins in local & remote tissue injury following ischemia & reperfusion. Amer. J. Path. 144:592–98 1994.
Greaing et al. Circulating adhesion molecules in disease Immunol. Today 17:506–12 1993.
Erbe et al. P-+E-selectin use common sites for carbohydrate ligand recognition & cell adhesion. J. Cell Biol. 120:1227–35 1993.
Goding Monoclonal antibodies: Principles & practice Prod. & application of mAb in cell Biol. Biochem. & immunol. 1986
Kearney Hybridomas & MAb. Fundamental. Immunol. 1984 751–66.
McDougal et al. Binding of The human retrovirus HTLV–III/LAV/ARV/HIV to the (by cty) molecule: Conformation Dependences, epitope mapping antibody inhibition, and potential for idio topic memory J. Immunol. 137:2937 1986.
Berg et al. Blood 85: 31–37 (1995).
Larsen et al. J Biol. Chem. 267:11104–11110 (1992).
Weitz–Schmidt et al. in Leukocyte Typing 5 Schlossman et al. (Eds.) Oxford University Press 1995 Chapter E6.24, pp. 1839–1840.
Lefer et al. Cardiovascular Research 28: 289–294(1994).

*Primary Examiner*—Christina Y. Chan
*Assistant Examiner*—Phillip Gambel
*Attorney, Agent, or Firm*—Townsend and Townsend and Crew LLP

[57] ABSTRACT

The invention provides monoclonal antibodies that specifically bind to P-selectin and to E-selectin. Many of the antibodies block the functional interactions of P-selectin and E-selectin with the irrespective counterreceptors.

12 Claims, 4 Drawing Sheets

CROSS-REACTING MONOCLONAL ANTIBODIES SPECIFIC FOR E- AND P-SELECTIN

BACKGROUND OF THE INVENTION

The ability of cells to adhere to one another plays a critical role in development, normal physiology, and disease processes such as inflammation. This ability is mediated by adhesion molecules, generally glycoproteins, expressed on cell membranes. Often, an adhesion molecule on one cell type will bind to another adhesion molecule expressed on a different cell type, forming a receptor counter-receptor pair. Three important classes of adhesion molecules are the integrins, selecting, and immunoglobulin (Ig) super family members (see Springer, *Nature* 346: 425 (1990); Osborn, *Cell* 62: 3 (1990); Hynes, *Cell* 69: 11 (1992), each of which is incorporated by reference in its entirety for all purposes). These molecules are vital to the interaction of leukocytes and platelets with themselves and with the extracellular matrix and vascular endothelium.

The selectin family of receptors-are so named because of their lectin-like domain and the elective nature of their adhesive functions. There are three known selectins L-selectin (also known as LECAM-1, Mel-14 or LAM-1 or CD62L), E-selectin (also called ELAM-1 or CD62E) and P-selectin (also known as CD62, CD62P, GMP140 or PADGEM). The selectins are highly homologous, containing a 120 amino acid (act) N-terminal lectin domain, an EGF-like domain, a variable number of multiple short consensus repeat (SCR) domains homologous to those found in complement regulatory proteins, followed by a transmembrane domain and short cytoplasmic tail. See Siegelman et al., *Science* 243: 1165–1172 (1989); Lasky et al., *Cell* 56: 1045–1055 Tedder et al., *J. Exp. Med.* 170: 123–133 (1989); Johnson et al., *Cell* 56: 1033–1044 (1989); Bevilacqua et al., *Proc. Natl. Acad. Sci. USA* 84: 9238–9242 (1987), Bevilacqua et al., *Science* 243: 1160–1165 (1989), Bevilacqua et al., *J. Clin. Invest.* 91: 379–387 (1993), Camerini et al., *Nature* 280: 496–498 (1989). The selectins have overlapping but distinct specificities for counterreceptors. See Bevilacqua et al., *J. Clin. Invest.* 91: 379–387 (1993); Feize, *Current Opinion in Struct. Biol.* 3: 701–710 (1993); Berg et al., *Biochem. Biophys. Res. Comm.* 184: 1048–1055 (1992); Foxall et al., *J. Cell Biol.* 117: 895–902 (1992); Larsen et al., *J. Biol. Chem.* 267: 11104–11110 (1992); Polley et al., *Proc. Natl. Acad. Sci. USA* 88: 6224–6228 (1991) (each of which is incorporated by reference in its entirety for all purposes).

P-selectin is constitutively expressed by both platelets and endothelial cells where it is stored in α-granules or Weibel-Palade bodies for rapid (seconds to minutes) translocation to the cell surface upon activation by, for example, thrombin or histamine (McEver et al., *J. Biol. Chem.* 250: 9799–9804 (1984); Hsu-Lin et al., *J. Biol. Chem.* 264: 8121–9126 (1984)). E-selectin is expressed by activated endothelial cells (e.g., after TNF-α or IL-1 stimulation for 6–8 hr). Its expression is controlled at the transcriptional level (Bevilacqua et al., 1987, supra; Bevilacqua et al., 1989, supra). P-selectin and E-selectin both bind to neutrophils and monocytes (Larsen et al., *Cell* 59: 305–312 (1989); Johnston et al., *Cell* 56: 1033–1044 (1989); Bevilacqua et al., 1987, supra; Bevilacqua et al., 1989, supra) as well as subsets of lymphocytes (Picker et al., *Nature* 349: 796–799 (1991); Shimizu et al., *Nature* 349: 799–802 (1991); Moore et al., *BBRC* 186: 173–181 (1992)). L-selectin is constitutively expressed by leukocytes, and mediates lymphocyte adhesion to peripheral lymph node high endothelial venules (HEV) (Gallatin et al., *Nature* 304: 30–34 (1983); Berg et al., *Immunol. Rev* 108: 5–18 (1989); Berg et al., *J. Cell. Biol.* 114: 343–349 (1991)), and neutrophil adhesion to cytokine-activated endothelial cells (Hallman et al., *Biochem. Biophys. Res. Comm.* 174: 236–243 (1991); Smith et al., *J. Clin. Invest.* 87: 609–618 (1991); Spertini et al., *J. Immunol.* 147: 2565–2573 (1991)). L-selectin is a counter-receptor on neutrophils for both E-selectin and P-selectin (Kishimoto et al., *Blood* 78: 805–811 (1990), Picker et al., *Cell* 66: 921 (1991)), although all three selecting probably have other counter-receptors as well. E-, P- and L-selectins mediate leukocyte-endothelial cell and platelet-leukocyte adhesive interactions during inflammation (Bevilacqua et al., 1993, supra). All three selectins have been demonstrated to participate in an initial "rolling" interaction of leukocytes with activated endothelium (von Andrian et al., *Proc. Natl. Acad. Sci. USA* 88: 7538–7542 (1991); Ley et al., *Blood* 77: 2553–2555 (1991); Abassi et al., *J. Clin. Invest.* 92: 2719–2730 (1993); Dore et al., *Blood* 82: 1308–1316 (1993); Jones et al., *Biophys. J.* 65: 1560–1569 (1993); Mayadas et al., *Cell* 74: 541–554 (1993)). This initial interaction precedes CD18-integrin-mediated adhesion and subsequent migration of neutrophils through the endothelium and into inflamed tissue sites (Lawrence et al., *Cell* 65: 859–873 (1991);von Andrian et al., *Am. J. Physiol.* 263: H1034–H1044 (1992)). Depending on the nature of inflammatory stimuli and time after initiation of inflammatory response either E- or P-selectin may be functionally dominant in promoting neutrophil-mediated tissue damage. In principle, antibodies or other antagonists of the selecting could abort the adhesion process, thereby preventing neutrophils from binding to the endothelium and from extravasating into tissues. A substantial number of antibodies specific for one of the selecting have been reported. Some of these antibodies have been reported to block binding of selecting to counterreceptors in vitro. Some of the antibodies have also been reported to block selectin-mediated interactions in animal models in vivo. For example antibodies to E-selectin have been reported to protect against neutrophil-mediated damage in an IgG complex model of lung injury in the rat (Mulligan et al., *J. Clin. Invest.* 88: 1396 (1991)).Antibodies to P-selectin have been reported to protect against acute lung injury induced by intravenous injection of cobra venom, factor (Mulligan et al., *J. Clin. Invest.* 90: 1600–1607 (1992)), as well as in a rat model of systemic endotoxemia (Coughlan et al., *J. Exp. Med.* 179: 329–334 (1994)). Antibodies to P-selectin have also been reported to be protective in a cat model of myocardial ischemia and reperfusion injury (Weyrich et al., *FASEB J.* 7: A785 (1993)).

Although some antibodies against E- and P-selectin have shown blocking activity, many, if not most, antibodies specific for E or P selectin are nonblocking (see, e.g., Bevilacqua et al., 1989, supra; Erbe et al., *J. Cell. Biol.* 119: 215–227 (1992)). That is, these antibodies bind to epitopes in the extracellular domains of E- or P-selectin that do not directly participate in counterreceptor binding of the subsequent cellular adhesion process. The prevalence of non blocking antibodies suggests that only small regions of the extracellular domain participate directly in binding or influence binding. Thus, de nova screening of antibodies generated against E- or P-selectin would be expected to generate mainly nonblocking antibodies.

Despite the large number of antibodies isolated to-date against the three selectins, there have been few reports of crossreacting antibodies that bind to more than one selectin. Crossreacting antibodies might be capable of aborting the inflammatory process at more than one level thereby providing more broadly useful therapeutic agents for neutrophil-mediated inflammatory conditions than antibodies specific for a single selectin. One antibody has been reported to crossreact with human E-selectin and dog L-selectin but not with the two selectins from the same species (Abassi et al., *J. Immunol.* 147: 2107–2115 (1991)). A second antibody has been reported to crossreact with human E- and L-selectins (Jutila et al., *J. Exp. Med.* 175: 1565–1573 (1992; WO/9324614). However, no antibody has been isolated that binds to both P- and E-selectin, much less blocks the functions of both of these molecules.

Accordingly, there is a need for antibodies that bind to both E- and P-selectin, preferably so as to block the capacity of both of these molecules to participate in adhesion reactors with counterreceptors. The present invention fulfills this and other needs.

SUMMARY OF THE INVENTION

The invention provides monoclonal antibodies that have a binding site that specifically binds to P-selectin and to E-selectin. For many such antibodies, specific binding of the antibody to the P-selectin inhibits binding of the P-selectin to a counterreceptor of P-selectin, and specific binding of the antibody to E-selectin inhibits binding of the E-selectin to a counterreceptor of E-selectin. Counterreceptors of E-selectin and P-selectin are expressed on the surface of cells such as HL-60 cells and neutrophils. Exemplary antibodies are designated 57C.29, 2C9.11 and 1D8.10. Many of the antibodies of the invention compete with an exemplified antibody for specific binding to P-selectin and to E-selectin. Some antibodies of the invention also specifically bind to L-selectin, whereas others do not. In addition to intact antibodies, the invention also provides binding fragments such as Fab, Fab', F(ab')$_2$, Fv or single-chain antibodies.

Some of the antibodies of the invention are mouse whereas others are humanized or human antibodies. A humanized antibody comprises a humanized heavy chain and a humanized light chain. The humanized light chain can comprise three complementarily determining regions (CDR1, CDR2 and CDR3) having amino acid sequences from the light chain of a mouse antibody selected from the group consisting of 5C7.29, 2C9.11 and 1D8.10, and having a variable region framework sequence substantially identical to a human light chain variable region framework sequence. The humanized heavy chain can comprise three complementarily determining regions (CDR1, CDR2 and CDR3) having amino acid sequences from the corresponding mouse antibody heavy chain and having a variable region framework sequence substantially identical to a human heavy chain variable region framework sequence. The humanized antibody specifically binds to the P-selectin with a binding affinity having a lower limit of about $10^7$ M$^{-1}$. The humanized antibody specifically binds to the E-selectin with a binding affinity having a lower limit of about $10^7$ M$^{-1}$.

In another aspect, the invention provides purified nucleic acid segments encoding a light or heavy chain variable region of one of the monoclonal antibodies discussed above The invention also provides stable cell lines capable of producing the antibodies described above. The stable cell lines comprise nucleic acid segments respectively encoding the heavy chain and light chain of an antibody described above. The segments are operably linked to first and second promoters to allow expression of the heavy and light chains.

The invention further provides pharmaceutical compositions comprising the antibodies described above and methods of treatment using the same. The methods of treatment are particularly effective for inflammatory diseases including conditions such as ischemia-reperfusion injury, adult respiratory distress syndrome, sepsis, psoriasis and autoimmune disease.

In another aspect, the invention provides methods of generating an antibody capable of blocking E-selectin and/or P-selectin mediated functions. The method comprises concurrently or consecutively immunizing a mammal with P-selectin and E-selectin. B-cells from the mammal are immortalized to generate immortalized cells producing antibodies. An immortalized cell is selected producing an antibody that specifically binds to E-selectin and to P-selectin.

The invention further provides methods of detecting E-selectin and P-selectin bearing cells in a biological sample suspected of containing the cells. The method comprises contacting the sample with an antibody as described above to form an immune complex with the E-selectin and/or P-selectin bearing cells. The presence of the immune complex is then detected to indicate the presence of the cells.

BRIEF DESCRIPTION OF THE DRAWINGS

FIGS. 3*a* to 3*d* Crossreactivity of 5C7.29 resides in a single monoclonal antibody. 5C7.29 antibody was incubated with excess of (a, c) parent L1-2 cells or (b, d) L1-2$^{P\text{-}selectin}$ transfectants, and resulting supernatants tested for reactivity with fresh samples of L1-2$^{P\text{-}selectin}$ (a, b) or L1-2$^{E\text{-}selectin}$ cells (c, d) by FACS analysis. This figure shows that L1-2$^{P\text{-}selectin}$ depletes reactivity for E-selectin FIG. 4 Monoclonal antibody 5C7.29 blocks binding of HL-60 (neutrophil-like) cells to TNF-α-activated HUVEC cells (expressing E-selectin). Average of four experiments.

DEFINITIONS

Figure 1A:
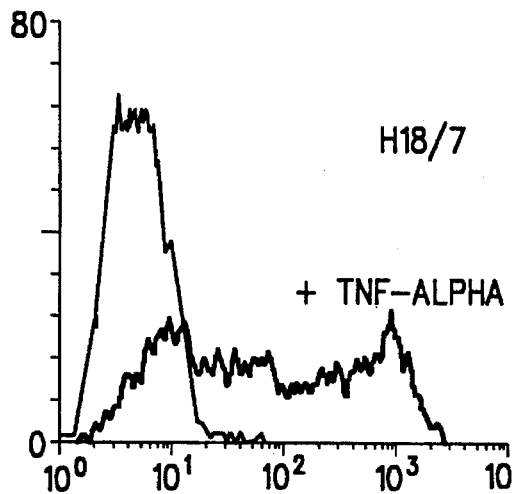
FIGS. 1*a* and 1*b* Crossreacting antibody 5C7.29 binds to naturally occurring human E-selectin. (a) Binding of known anti-E-selectin antibody H18/7 to activated (black histograms) and resting (grey histograms) HUVEC cells. (b)Binding of crossreacting antibody 5C7.29 to activated and resting HUVEC cells. FACS fluorescence intensity is indicated by the X axis.

The term "substantial identity" or "substantial homology" means that two peptide sequences, when optimally aligned, such as by the programs GAP or BESTFIT using default gap weights, share at least 65 percent sequence identity preferably at least 80 or 90 percent sequence identity, more preferably at least 95 percent sequence identity or more (e.g., 99 percent sequence identity). Preferably, residue positions which are not identical differ by conservative amino acid substitutions.

The term "substantially pure" or "isolated" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent by weight of all macromolecular species present in the composition. Most preferably, the object species is purified to essential homogeneity (contaminant species cannot be detected in the composition by conventional detection methods) wherein the composition consists essentially of a single macromolecular species.

"Immunoglobulin," "antibody" or "antibody peptide(s)" refers to an intact antibody, or a binding fragment thereof that competes with the intact antibody for specific binding. Binding fragments are produced by recombinant DNA techniques, or by enzymatic or chemical cleavage of intact immunoglobulins. Binding fragments include Fab, Fab', F(ab')$_2$, Fv and single-chain antibodies. An antibody other than a "bispecific" or "bifunctional" antibody is understood to have each of its binding sites identical.

An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term epitope includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

An antibody is said to specifically bind an antigen when the dissociation constant is $\leq 1$ μM, preferably $\leq 100$ nM and most preferably $\leq 10$ nM.

The term patient includes human and veterinary subjects.

The term P-selectin counterreceptor denotes a protein other than an antibody that specifically binds to P-selectin at least in part by noncovalent bonds. Specific binding maintains cells respectively bearing receptor and counterreceptor in physical proximity and may also transduce a change in physical or functional phenotype in either of the cells or both. Other selectin counterreceptors are analogously defined.

DESCRIPTION OF THE PREFERRED EMBODIMENT

Antibodies of the Invention

The invention provides antibodies that crossreact, i.e., specifically bind, with E-selectin and P-selectin Preferred antibodies block the functions of both of these molecules.

A. General Characteristics of Antibodies

The basic antibody structural unit is known to comprise a tetramer. Each tetramer is composed of two identical pairs of polypeptide chains, each pair having one "light" (about 25 kDa)and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as gamma, mu, alpha, lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids (See generally, *Fundamental Immunologic* (Paul, W., ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hyper variable regions, also called complementarily determining regions or CDRs. The CDRs from the two chains of each pair are aligned by the framework regions, enabling binding to a specific epitope From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196: 901–917 (1987); Chothia et al., *Nature* 342: 878–883 (1989)

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79: 315–321 (1990), Kostelny et al., *J. Immunol.* 148, 1547–1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

B. Binding Specificity and Affinity

The immunoglobulins (or antibodies) of the invention exhibit specific binding to both P- and E-selectins. That is, a single binding site on an antibody has affinity for both P- and E-selectin. Thus, the antibodies bind to epitopes that are common to both molecules. The antibodies bind to the natural and/or recombinant human forms for P- and E-selectin (see Johnston et al., 1989, supra; Bevilacqua et al., 1989 supra). Some antibodies may also bind P- and/or E-selectin from non human species. Some of the antibodies also specifically bind to L-selectin (preferably human L-selectin (see Tedder, EPA386, 906 (1990))whereas other antibodies of the invention do not. Surprisingly, the common epitopes bound by the crossreacting antibodies of the invention are also epitopes important for both E- and P-selectin to interact with their counterreceptors on activated leukocytes, such as neutrophils. Thus, most crossreacting antibodies of the invention block the functional interactions of E-selectin or P-selectin and usually those of both of these molecules. Some crossreacting antibodies also block the functional interactions of L-selectin whereas others do not.

Blockage of P-selectin-mediated functions can be demonstrated in vitro. In vitro assays measure the capacity of an antibody to inhibit binding of P-selectin to a counterreceptor. Suitable sources of P-selectin for such assays are purified P-selectin (or an extracellular domain thereof), cells transfected with P-selectin, activated endothelial cells or platelets. Suitable sources of counterreceptor are leukocytes, neutrophils, monocytes, or HL-60 cells (ATCC CCL240)and appropriate cell lines transfected with L-selectin. Neutrophils can be isolated from whole blood (preferably human blood) by Ficoll-Hypaque gradient centrifugation. Neutrophils are usually pretreated with rabbit serum to block Fc receptors before adding to a binding assay. When both components in the biding assay are cellular, binding can be assayed microscopically or by flow cytometry. See Kishimoto et al., supra. When one or both components is a purified protein, one component is usually immobilized to a solid phase and the other labelled. Binding is then assayed from label bound to the solid phase. Usually, the antibody is preincubated with the source of P-selectin before adding the source of counterreceptor to the incubation mixture. Blocking activity is shown when an excess of antibody, i.e., 5-fold, 10-fold or up to 100-fold, substantially inhibits binding of P-selectin to its counterreceptor. The precise degree of inhibition will depend on the assay used. In an assay that measures inhibition of platelet binding to HL-60 cells, an excess of P-selectin blocking antibodies typically exhibits at least 50, 60, 70, 80 or 90% and usually about 80–90% inhibition.

The binding specificity of many blocking antibodies of the invention is further defined by their capacity to bind P-selectin in the complete or substantial absence of $Ca^{++}$ (e.g., in the presence of 2 mM EDTA (a calcium chelator)and the absence of $Ca^{++}$ in an in vitro assay). By contrast, most blocking antibodies against P-selectin isolated to date require $Ca^{++}$ for activity. See Geng et al., *J. Biol. Chem.* 266: 22313–22318 (1991). Antibodies requiring a $Ca^{++}$ cofactor for blocking activity may be less effective in in viva conditions where levels of $Ca^{++}$ are expected to fluctuate.

The capacity of the antibodies of the invention to block E-selectin-mediated functions can be demonstrated by analogous in vitro assays to those employed to show blocking of P-selectin mediated functions. Suitable sources of E-selectin are mammalian cell lines transfected with E-selectin activated endothelial cells, as well as purified E-selectin (or extracellular domains thereof). If the assay is performed using purified E-selectin, the E-selectin can be immobilized to a solid support. Suitable sources of counterreceptors to E-selectin are leukocytes, neutrophils, monocytes, and HL-60 cells and appropriate cell lines transfected with L-selectin. The degree of binding inhibition will again depend on the components in the assay. In an assay that measures binding between activated endothelial cells and HL-60 cells, the antibodies of the invention, when present in excess, typically exhibit at least about 20, 40, 60, 80% inhibition or more typically about 25–75% or 50% inhibition. The capacity of antibodies to block L-selectin mediated functions can be demonstrated in a variety of in vitro assays. See, e.g., copending application Ser. Nos. 08/160,516, filed Nov. 30, 1993and 08/160,074, filed Nov. 30, 1993 (incorporated by reference in their entirety for all purposes). A simple visual assay for detecting such interaction has been described by Kishimoto et al., supra. Briefly, monolayers of human umbilical vein cells are stimulated with IL-1. Neutrophils, with or without pretreatment with the antibody under test, are added to the monolayer under defined conditions, and the number of adhering neutrophils is determined microscopically. In one method, the neutrophils are obtained from human leukocyte adhesion deficient patients. See Anderson et al., *Ann. Rev. Med.* 38: 175 (1987). The neutrophils from such patients lack integrin receptors, whose binding to neutrophils might obscure the effects of blocking L-selectin binding.

Preferred antibodies selectively bind a functional epitope on P- and E-selectin molecules associated with a response to tissue injury and inflammation. Binding of the antibodies to a functional epitope on P-selectin and E-selectin effectively inhibits adhesion of leukocytes to the activated vascular endothelium and/or to activated platelets in vivo. Preferred antibodies impair the adhesion of leukocytes to the activated vascular endothelium to prevent or inhibit an inflammatory and/or thrombotic condition.

In vivo blocking efficacy can be demonstrated in the same animal models that have been used to show efficacy for antibodies specific for a single adhesion molecule. For example, Mulligan et al., 1991, 1992, supra, describe rat models to test the efficacy of antibodies in protecting against lung injury; Coughlan et al., 1994, describe a rat model for testing the efficacy of antibodies in treatment of systemic endotoxemia; and Weyrich et al., supra, describe a cat model for testing the protective effect of antibodies in myocardial ischemia and reperfusion injury. Other animal models for various inflammatory diseases and disorders are described by Arfors et al., *Blood* 69: 338 (1987) (skin lesions); Tuomanen et al., *J. Exp. Med.*70: 959 (1989) (brain edema and death produced by bacterial meningitis); Lindbom et al., *Clin. Immunol. Immunopath.* 57: 105 (1990) (tissue edema associated with delayed-type hypersensitivity reactions); Wegner et al., *Science* 247: 456 (1990) (airway hyperresponsiveness in allergic asthma); Goldman et al., *FASEB J.* 5: A509 (1991) (remote lung injury following aspiration); Gundel et al., *J. Clin. Invest.* 88: 1407 (1991) (late-phase bronchoconstriction following antigen challenge); Hutchings et al., *Nature* 346: 639 (1990) (diabetes); Flavin et al., *Transplant, Proc.* 23: 533 (1991) (cardiac allograft survival; Wegner et al., *Am. Rev. Respir. Dis.* 143: A544 (1991) (lung damage and dysfunction secondary to oxygen toxicity); Cosimi et al., *J. Immunol.* 144: 4604 (1990) (renal allograft rejection); Jasin et al., *Arthritis. Rheum.* 33: S34 (1990) (antigen-induced arthritis); Thomas et al., *FASEB J.* 5: A509 (1991) (vascular injury and death in endotoxic shock); Bucky et al., *Proc. Am. Burn Assoc.* 23: 133 (1991) (burns); Hernandez et al., *Am. J. Physiol.* 253: H699 (1987) (permeability edema following ischemia reperfusion (IR) of intestine); Winquist et al., *Circulation* 82: III (1990); Ma et al., *Cir. Res.* 82: III: (1990) (myocardial damage following myocardial infarction); Mileski et al., *Surgery* 108: 206 (1990) (vascular and tissue damage following hemorrhagic shock and resuscitation); Clark et al., *Stroke* 22: 877 (1991) (central nervous system damage following I/R of the spinal cord); Mileski et al., *Proc. Am Burn Assoc.* 22: 164 (1990) (edema and tissue damage following frostbite and rewarming); Simpson et al., Circulation 81: 226 (1990) (infarct size following I/R of myocardium). Preferred antibodies show efficacy in at least one and usually several of these inflammatory and thrombotic diseases and conditions Many of the blocking antibodies of the invention show the same or similar binding specificity as one of the exemplary antibodies designated 5C7.29, 2C9.11 and 1D8.10. That is, the antibodies compete with at least one of the exemplified antibodies for specific binding to E- and/or P-selectin. The E- and P-selectin used in the test is preferably human, and may be natural or recombinant. Competition between antibodies is determined by an assay in which the immunoglobulin under test inhibits specific binding of a reference antibody (e.g., 5C7.29) to an antigenic determinant on a P-selectin and/or E-selectin molecule. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9: 242–253 (1983)); solid phase direct biotin-avidin EIA (see Kirkland et al., *J. Immunol.* 137: 3614–3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al, *Molec. Immunol.* 25 (1): 7–15 (1988)); solid phase direct biotin-avidin EIA (Cheung et al., *Virology* 176: 546–552 (1990)) and direct labeled RIA (Moldenhauer et al., *Scand. J. Immunol.* 32: 77–82 (1990)). Typically, such an assay involves the use of purified P-selectin or E-selectin bound to a solid surface or cells bearing either of these, an unlabelled test immunoglobulin and a labelled reference immunoglobulin. Competitive inhibition is measured by determining the amount of label bound to the solid surface or cells in the presence of the test immunoglobulin. Usually the test immunoglobulin is present in excess. Antibodies identified by competitor assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess it will inhibit specific binding of a reference antibody to P-selectin and/or E-selectin by at least 50 or 75%.

The antibodies of the invention usually edit specific binding affinity for P-selectin and E-selectin of greater than or equal to about $10^6$, $10^7$, $10^8$, $10^9$, or $10^{10}$ $M^{-1}$. However, antibodies do not necessarily show the same specific binding affinity for each of these ligands. Usually the upper limit of binding affinity of the antibodies is within a factor of about three, five or ten of that of one of the exemplified antibodies. Often the lower limit of binding affinity is also within a factor of about three, five or ten of that of the exemplified antibodies. The term "about" encompasses the degree of experimental error that may typically occur in the measurement of binding affinities.

A hybridoma producing the 5C7.29 antibody has been deposited with the American Type Culture Collection, 12301 Parklawn Dr., Rockville, Md. under the Budapest Treaty on May 25, 1994 and given the Accession No. ATCC CRL 11640. The production of this antibody is described in Example 1.

C. Production of Antibodies (1) Nonhuman Antibodies

Mouse, or other nonhuman antibodies crossreactive with P and E-selectin can be obtained using a variety of immunization strategies. In some strategies, nonhuman animals (usually non human mammals), such as mice, are immunized with E- and P-selectin antigens, either concurrently or consecutively. In other strategies, nonhuman animals are immunized with only one of these antigens. Preferred immunogens are cells stably transfected with P-selectin or E-selectin and expressing these molecules on their cell surface Other preferred immunogens include P- and E-selectin proteins or epitopic fragments of P- and P-selectin containing the segments of these molecules that bind to the exemplified crossreacting antibodies.

Mouse or non-human antibodies crossreactive with all three selectins, i.e., P-, E-, and L-selectin, can be generated by similar strategies. Briefly, mice are immunized either simultaneously or sequentially with cells stably transfected with either P-, E-, or L-selectin, or purified selection proteins or epitopic fragments thereof.

Antibody-producing cells obtained from the immunized animals are immortalized and selected for the production of an antibody which specifically binds to multiple selectins. See generally, Harlow & Lane, *Antibodies, A Laboratory Manual* (C.S.H.P. N.Y., 1988) (incorporated by reference for all purposes). The binding assays for the different selectins can be performed separately or concurrently. Concurrent analysis is conveniently performed by two-color FACS screening after incubation of hybridomas supernatants to cells transfected with selectins. For example, two populations of cells respectively expressing E- and P-selectin are differentially labelled with a first label and tested for capacity to bind hybridomas supernatants. Binding is detected using an appropriate secondary antibody bearing a second label. This scheme is readily extendible to allow simultaneous detection of binding to all three selectins by differentially labelling three populations of cells respectively expressing E-, P- and L-selectin with different intensities of the first label. Alternatively, separate screening for E-selectin, P-selectin and, if desired, L-selectin binding, can be achieved by single color FACS analysis of supernatant binding to transfectant cells or by binding assay to immobilized E, P, or L-selectin. Crossreacting antibodies are then further screened for their capacity to block functional properties of E-, P- and L-selectin using the in vitro and in viva assays described above. Most antibodies that crossreact with P-selectin E-selectin also block the functional capacity of both of these molecules to interact with a counterreceptor.

2) Humanized Antibodies

The invention provides humanized antibodies having similar binding specificity and affinity to selected mouse or other non human antibodies. Humanized antibodies are formed by linking the CDR regions of non-human antibodies to human framework and constant regions by recombinant DNA techniques. See Queen et al., *Proc. Natl. Acad. Sci. USA* 86: 10029–1033 (1989) and WO90/07861 (incorporated by reference in their entirety for all purposes). The humanized immunoglobulins have variable region framework residues substantially from a human immunoglobulin (termed an acceptor immunoglobulin) and complementarily determining regions substantially from a mouse immunoglobulin described above, e.g., the 5C7.29 antibody (referred to as the donor immunoglobulin ). The constant region(s), if present, are also substantially from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues can be selected for substitution based on their possible influence on CDR conformation and/or binding to antigen. Investigation of such possible influences is by modeling examination of the characteristics of the amino acids at particular locations, or empirical observation of the effects of substitution or mutagenesis of particular amino acids For example, when an amino acid differs between a murine 5C7.29 variable region framework residue and a selected human variable region framework residue, the human framework amino acid should usually be substituted by the equivalent framework amino acid from the mouse antibody when it is reasonably expected that the amino acid:

(1) contacts antigen directly, (2) is adjacent to a CDR region in the sequence or (3) otherwise interacts with a CDR region (e.g., is within about 4–6 Å of a CDR region).

Other candidates for substitution are acceptor human framework amino acids that are unusual for a human immunoglobulin at that position. These amino acids can be substituted with amino acids from the equivalent position of the donor antibody or from the equivalent positions of more typical human immunoglobulins. The variable region frameworks of humanized immunoglobulins usually show at least 85% sequence identity to a human variable region framework sequence or consensus of such sequences.

(3) Human Antibodies

In another aspect of the invention, human antibodies cross-reactive with E-selectin and P-selectin are provided These antibodies are produced by a variety of techniques described below. Some human antibodies are selected by competitive binding experiments, or otherwise, to have the same epitope specificity as an exemplified mouse antibody, such as 5C7.29. Such antibodies are particularly likely to share similar therapeutic properties.

a. Trioma Methodology

The basic approach and an exemplary cell fusion partner, SPAZ-4, for use in this approach have been described by Oestberg et al., *Hybridoma* 2: 361–367 (1983); Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non- antibody -producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

The B-lymphocytes are obtained from the blood, spleen, lymph nodes or bone marrow of a human donor. In vivo immunization of a living human with E- and/or P-selectin is usually undesirable because of the risk of initiating a harmful response. Thus, B-lymphocytes are usually immunized in vitro with an E-selectin and/or P-selectin or an antigenic fragment of either of these, or a cell bearing either of these. Specific epitopic fragments consisting essentially of the amino acid segments that bind to one of the exemplified murine antibodies are preferred for in vitro immunization. B-lymphocytes are typically exposed to antigen for a period of 7–14 days in a media such as RPMI-1640 (see Engleman, supra) supplemented with 10% human serum. The immunized B-lymphocytes are fused to a xenogeneic hybrid cell such as SPAZ-4 by well known methods. For example, the cells are treated with 40–50% polyethylene glycol of MW 1000–4000, at about 37 degrees, for about 5–10 min. Cells are separated from the fusion mixture and propagated in media selective for the desired hybrids (e.g., HAT or AH). Clones secreting antibodies having the required binding specificity are identified by assaying the trioma culture medium for the ability to bind to E- and P-selectin using the same methods as discussed above for nonhuman antibodies. Triomas producing human antibodies having the desired specificity are subcloned by, e.g., the limiting dilution technique and grown in vitro in culture medium.

Although triomas are genetically stable they may not produce antibodies at very high levels. Expression levels can be increased by cloning antibody genes from the trioma into one or more expression vectors, and transforming the vector into a cell line such as the cell lines discussed, infra, for expression of recombinant or humanized immunoglobulins.

b. Transgenic Non-Human Mammals

Human antibodies crossreactive with P and E-selectin can also be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both in activation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO 93/12227 (1993); Kucherlapati, WO 91/10741 (1991) (each of which is incorporated by reference in its entirety for all purposes) Tranegenic mice are particularly suitable. Crossreacting P-selectin/E-selectin human antibodies are obtained by immunizing a transgenic non human mammal, such as described by Lonberg or Kucherlapati, supra, according to the same strategy as discussed for a non transgenic non human animal (section I. C. (1)). Monoclonal antibodies are prepared by, e.g., fusing B-cells from such mammals to suitable myeloma cell lines using conventional Kohler-Milstein technology.

c. Phage Display Methods

A further approach for obtaining human crossreacting antibodies to E- and P-selectin is to screen a DNA library from human B cells as described by Dower et al., WO91/17271 and McCafferty et al., WO92001047 (each of which is incorporated by reference in its entirety for all purposes). In these methods, libraries of phage are produced in which members display different antibodies on their outer surfaces. Antibodies are usually displayed as Fv or Fab fragments. Phage displaying antibodies are selected by affinity enrichment for binding to either P or E-selectin. Phage identified by the initial screen are then further screened for cross reaction with the other ligand.

In a variation of the phage-display method, human antibodies having the binding specificity of a selected marine antibody can be produced. See Winter, WO 92/20791. In this method, either the heavy or light chain variable region of the selected murine antibody (e.g., 5C7.29) is used as a starting material. If, for example, a light chain variable region is selected as the starting material, a phage library is constructed in which members displays the same light chain variable region (i.e., the murine starting material) and a different heavy chain variable region. The heavy chain variable regions are obtained from a library of rearranged human heavy chain variable regions. A phage showing strong specific binding for P- and E-selectin (e.g., at least $10^8$ and preferably at least $10^9 M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable region s are obtained from a library of rearranged human variable light chain regions. Again, phage showing strong specific binding for P- and E-selectin are selected. The phage display the variable regions of completely human antibodies that crossreact with E- and P-selectin. These antibodies usually have the same or similar epitope specificity as the murine starting material (e.g., 5C7.29).

D. Bispecific Antibodies

The invention also provides bispecific or bifunctional antibodies that have one binding site that specifically binds to P-selectin and E-selectin and a second binding site that specifically binds to a second moiety. In bispecific antibodies, one heavy and light chain pair is usually from a cross reacting antibody and the other pair from an antibody raised against another epitope. This results in the property of multi-functional valency, i.e., ability to bind at least two different epitopes simultaneously, one of which is the epitope to which the anti P-selectin /E-selectin crossreacting antibody binds. The other epitope could be e.g., an epitope on L-selectin E. Other Therapeutic Agents Having produced an antibody having desirable properties, such as 5C7.29 and the other exemplified antibodies, other non antibody agents having similar binding specificity/and or affinity can be produced by a variety of methods. For example, Fodor et al., U.S. Pat. No. 5,143,854, discuss a technique termed LSIPS™ in which a diverse collection of short peptides are formed at selected positions on a solid substrate. Such peptides could then be screened for binding to an epitopic fragment recognized by 5C7.29, optionally in competition with the 5C7.29. Libraries of short peptides can also be produced using phage-display technology, see, e.g., Devlin WO91/18980. The libraries can be screened for binding to an epitopic fragment recognized by e.g., 5C7.29, optionally in competition with 5C7.29.

II. Nucleic Acids

The genes encoding the heavy and light chains of immunoglobulins produced by hybridoma or trioma cell lines secreting crossreacting antibodies are cloned according to methods described in Sambrook et al., *Molecular Cloning: A Laboratory Manual*, 2nd ed. (Cold Spring Harbor, N.Y., 1989); Berger & Kimmel, Methods in Enzymology, Volume 152, *Guide to Molecular Cloning Techniques* (Academic Press, Inc., San Diego, Calif., 1987); Co et al., *J. Immunol.* 148:1149 (1992). For example, genes encoding heavy and light chains are cloned from a hybridoma's genomic DNA or cDNA produced by reverse transcription of RNA. Cloning is accomplished by conventional techniques including the use of PCR primers that hybridize to the sequences flanking or overlapping the genes, or segments of genes, to be cloned.

Typically, recombinant constructs comprise DNA segments encoding a complete human immunoglobulin heavy chain and/or a complete human immunoglobulin light chain of an immunoglobulin expressed by a hybridoma or trioma cell line. Alternatively, DNA segments encoding only a portion of the primary antibody genes are produced, which portions possess binding and/or effect or activities. Other recombinant constructs contain segments of immunoglobulin genes fused to segments of other immunoglobulin genes, particularly segments of other human constant region sequences (heavy and/or light chain). Human constant region sequences can be selected from various reference sources, including those listed in Kabat et al., supra.

DNA segments encoding crossreacting P-selectin/E-selectin antibodies can be modified by recombinant DNA techniques such as site-directed mutagenesis (see Gillman & Smith, *Gene* 8: 81–97 (1979); Roberts et al., *Nature*, 328: 731–734 (1987). Such modified segments will usually retain antigen binding capacity and/or effector function. Moreover the modified segments are usually not so far changed from the original sequences to prevent hybridization to these sequences under stringent conditions. The modified segments will usually encode an immunoglobulin showing substantial sequence identity to a reference immunoglobulin from which it was derived. Because, like many genes, immunoglobulin genes contain separate functional region s, each having one or more distinct biological activities, the genes may be fused to functional region s from other genes to produce fusion proteins (e.g., immunotoxins) having novel properties or novel combinations of properties.

The recombinant polynucleotide constructs will typically include an expression control sequence operably linked to the coding sequences, including naturally-associated or heterologous promoter region s. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors will contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among other s, promoters from alcohol dehydrogenase, isocytochrome C, and enzymes responsible for maltose and galactose utilization Mammalian cells are a preferred host for expressing nucleotide segments encoding immunoglobulin s or fragments thereof. See Winnacker, *From Genes to Clones*, (VCH Publishers, N.Y., 1987). A number of suitable host cell lines capable of secreting intact heterologous proteins have been developed in the art, and include CHO cell lines, various COS cell lines, HeLa cells, L cells and myeloma cell lines. Preferably, the cells are non human. Expression vectors for these cells can include expression control sequences, such as an origin of replication, a promoter, an enhancer (Queen et al., *Immunol. Rev.* 89: 49 (1986)), and necessary processing information sites, such as ribosome binding sites, RNA splice sites, polyadenylation sites, and transcriptional terminator sequences. Preferred expression control sequences are promoters derived from endogenous genes, *cytomegalovirus* SV40, adenovirus, *bovine papillomavirus*, and the like. See Co et al., *J. Immunol.* 148:1149 (1992).

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation lipofection, biolistics or viral-based transfection may be used for other cellular hosts. Other methods used to transform mammalian cells include the use of polybrene, protoplast fusion, liposomes, electroporation, and microinjection (see generally, Sambrook et al., supra).

Once expressed, crossreacting immunoglobulin s of the invention can be purified according to standard procedures of the art, including HPLC purification, column chromatography, gel electrophoresis and the like (see generally, Scopes; *Protein Purification* (Springer-Verlag, N.Y., 1982)).

III. Epitone Mapping

The P-selectin epitope(s) bound by the 5C7.29 or other crossreacting antibody is determined by providing a family of fragments containing different amino acid segments from P-selectin. Each fragment typically comprises at least 4, 6, 8, 10, 20, 50 or 100 contiguous amino acids. The family of polypeptide fragments cover much or all of the amino acid sequence of the extracellular domain of a P-selectin polypeptide. Members of the family are tested individually for binding to e.g., the 5C7.29 antibody. The smallest fragment that can specifically bind to the antibody under-test delineates the amino acid sequence of the epitope recognized by the antibody. The E-selectin epitope bound by the antibody is mapped by an analogous strategy using a family of peptides from E-selectin. The respective epitopes on P and E-selectin are expected to map to segments of these molecules showing a high degree of sequence identity. The epitopic fragments are useful as immunogens for generating further crossreacting antibodies. The epitopic fragments are also useful as therapeutic agents that agonize or antagonize the function of P or E-selectin.

IV. Pharmaceutical Compositions

The pharmaceutical composition s for use in the therapeutic methods discussed infra, typically comprise an active agent, such as crossreacting E-selectin/P-selectin antibody, dissolved in an acceptable carrier, preferably an aqueous carrier. Some composition s contain a cocktail of multiple active agents, for example, a crossreacting antibody and a thrombolytic agent. A variety of aqueous carriers can be used, e.g., water, buffered water, phosphate buffered saline (PBS), 0.4% saline, 0.3% glycine, human albumin solution and the like. These solutions are sterile and generally free of particulate matter. The compositions man contain pharmaceutical acceptable auxiliary substances as required to approximate physiological conditions such as pH adjusting and buffering agents, toxicity adjusting agents and the like, for example, sodium acetate, sodium chloride, potassium chloride, calcium chloride and sodium lactate The concentration of antibody in these formulations can vary widely, i.e., from less than about 0.005%, usually at least about 1% to as much as 15 or 20% by weight and will be selected primarily based on fluid volumes, viscosities, and so forth, in accordance with the particular mode of administration selected.

Thus, a typical pharmaceutical composition for injection could be made up to contain 1 ml sterile buffered water, and 1–10 mg of immunoglobulin. A typical composition for intravenous infusion could be made up to contain 250 ml of sterile Ringer's solution, and 150 mg of antibody. Methods for preparing parenterally administrable composition s are described in *Remington's Pharmaceutical Science* (15th ed., Mack Publishing Company, Easton, Pa. 1980), which is incorporated by reference in its entirety for all purposes Therapeutic agents of the invention can be frozen or lyophilized for storage and reconstituted in a suitable carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate.

V. Therapeutic Methods

The antibodies of the present invention are useful for treatment of inflammatory diseases and conditions, especially those which are mediated by neutrophils. The dual specificity of the antibodies leads to the inhibition of inflammatory events mediated by either P- or E-selectin For example, the antibodies are suitable for therapeutic and prophylactic treatment of ischemia-reperfusion injury caused by myocardial infarction, cerebral ischemic event (e.g., stroke), renal, hepatic or splenic infarction brain surgery, lung injury, shock, cardiac surgery (e.g., coronary artery bypass), elective angioplasty, and the like. Other preferred applications are the treatment of sepsis, adult respiratory distress syndrome, and multiple organ failure. The antibodies are also useful for treating injury due to trauma, burns, frostbite or damage to the spinal cord. The antibodies will also find use in treating autoimmune diseases including rheumatoid arthritis, systemic lupus erythematosus, multiple sclerosis, type I diabetes and uveitis, in treating inflammatory diseases of the skin such as psoriasis, and in treating meningitis and encephalitis. The antibodies are also useful for treating allergic rhinitis, asthma and anaphylaxis. Other typical applications are the prevention and treatment of organ transplant rejection and graft-versus-host disease.

The pharmaceutical composition s containing the antibodies are particularly useful for parenteral administration, i.e., subcutaneously, intramuscularly or intravenously. The antibodies of the invention may also be administered, typically for local application, by gavage or ravage, intraperitoneal injection, ophthalmic ointment, topical ointment, intracranial injection (typically into a brain ventricle), intrapericardiac injection, or intrabursal injection.

The compositions containing the present antibodies or a cocktail thereof can be administered for prophylactic and/or therapeutic treatments. In therapeutic applicators composition s are administered to a patient already suffering from an inflammatory disease, in an amount sufficient to cure or at least partially arrest the disease and its complications. An amount adequate to accomplish this is defined as a "therapeutically effective dose." Amounts effective for this use will depend upon the severity of the disease and the general state of the patient's own immune system, but generally range from about 1 to about 200 mg of antibody per dose, with dosages of from 5 to 80 mg per patient being more commonly used. Dosing schedules will vary with the disease state and status of the patient, and will typically range from a single bolus dosage or continuous infusion to multiple administration per day (e.g., every 4–6 hours), or as indicated by the treating physician and the patient's condition. In life-threatening or potentially life-threatening situations, it is possible and may be felt desirable by the treating physician to administer substantial excesses of these antibodies.

In prophylactic applications, compositions containing the present antibodies or a cocktail thereof are administered to a patient not already suffering from a particular disease to enhance the patient's resistance. Such an amount is defined to be a "prophylactically effective dose." In this use, the precise amounts again depend upon the patient's state of health and general level of immunity, but generally range from 1 to 80 mg per dose. Preferred prophylactic uses are for the prevention of adult respiratory distress syndrome in patients already suffering from sepsis or trauma; prevention of organ transplant rejection; and prevention of reperfusion injury in patients suffering from ischemia. In seriously ill patients, dosages of about 50 to 150 mg of humanized or human immunoglobulin per administration are frequently used, and larger dosages may be indicated Single or multiple administrations of the composition s can be carried out with dose levels and pattern being selected by the treating physician. In any event, the pharmaceutical formulations should provide a quantity of the antibody (ies) of this invention sufficient to treat the patient effectively.

The antibodies can also be used in combination with other antibodies, particularly antibodies reactive with different adhesion molecules. For example, suitable antibodies include those specific for CD11a, CD11b, CD18, L-selectin, and ICAM-1. Other suitable antibodies are those specific for lymphokines, such as IL-1, IL-2 and IFN-γ, and their receptors. The antibodies of the invention can also be administered in conjunction with chemotherapeutic agents Suitable agents include non-steroidal anti- inflammatory drugs and corticosteroids, but numerous additional agents (e.g., cyclosporin) can also be used.

In some therapeutic methods of ischemia-reperfusion therapy, crossreacting antibodies are used in combination with thrombolytic agents. In previous methods, patients with myocardial infarction or unstable angina are often treated by opening the occluded coronary artery. Reopening of the obstructed coronary artery can be achieved by administration of thrombolytic agents which lyse the clot causing the obstruction, and which, thereby, restore coronary blood flow. Reperfusion of the vessel can also be achieved by percutaneous transluminal coronary angioplasty (PTCA) by means of balloon dilation of the obstructed and narrowed segment of the coronary artery. However, restoration of coronary blood flow leads to ischemia-reperfusion injury in prior methods.

In the present methods, ischemia-reperfusion injury is reduced or prevented by combination of a thrombolytic agent or of PTCA with crossreacting E-selectin/P-selectin antibodies. Antibodies are usually administered prophylactically before, or at the same time as, administration of thrombolytic agents or initiation of PTCA. Further doses of antibody are then often administered during and after thrombolytic or angioplastic treatment. The interval between prophylactic administration of the antibodies and initiation of thrombolytic or angioplastic treatment is usually 5–60 mins, preferably 5–30 min, and most preferably 5–10 min. The antibodies are administered parentally, preferably by intravenous injection, in doses of 0.01–10 mg/kg body weight, preferably of 0.14–5 mg/kg and most preferably of 0.3–3 mg/kg. The antibodies can be given as an intravenous bolus injection, e.g., over 1–5 min., as repeated injections of smaller doses, or as an intravenous infusion. The bolus injection is especially useful for the prophylactic dose or in an emergency. Further doses of antibodies can be repeated (e.g., every 4–24 hr) during and after thrombolytic or angioplastic treatment of acute myocardial infarction at the same proportions as described above to achieve optimal plasma levels of the antibody.

Thrombolytic agents are drugs having the capacity, directly or indirectly, to stimulate dissolution of thrombi in vivo. Thrombolytic agents include tissue plasminogen activator (see EP-B 0 093 619), activate, alteplase, duteplase, silteplase, streptokinase, anistreplase, urokinase heparin, warfarin and coumarin. Additional thrombolytic agents include saruplase and vampire bat plasminogen activator. See Harris, *Protein Engineering* 6: 449–458 (1987); PCT/EP 90/00194; U.S. Pat. No. 4,970,159. Thrombolytic agents are administered to a patient in an amount sufficient to partially disperse, or prevent the formation of, thrombi and their complications. An amount adequate to accomplish this is defined as a "therapeutically effective dose" or "efficacious dose." Amounts effective for this use will depend upon the severity of the condition, the general state of the patient, the route of administration and combination with other drugs.

Often, therapeutically effective doses of thrombolytic agents and administration regimens for such agents with crossreacting antibodies to E- and P-selectin are those approved by the FDA for independent uses of thrombolytic agents, e.g., 100 mg of alteplase or 1.5 million IU of streptokinase.

VI. Methods of Diagnosis

The monoclonal antibodies of the present invention are useful for diagnosing the inflammatory conditions discussed above and monitoring the treatment thereof. The antibodies detect P-selectin and E-selectin in a tissue sample such as serum or endothelial cells, e.g., by ELISA or RIA; The presence of either selectin is diagnostic of inflammation Selectin levels may be employed as a differentiation marker to identify and type cells of certain lineages and developmental origins.

In such procedures, the antibody can be labelled directly (e.g., by radioactive or fluorescent label) and immune complexes detected via the label. Usually, however the antibody is unlabelled and the desired antigen-monoclonal antibody complex is detected with an enzyme-conjugated antibody against the monoclonal antibody. Diagnosis can also be achieved by in vivo administration of a labelled crossreacting P-selectin/E-selectin antibody and detection by in vivo imaging. The concentration of antibody administered should be sufficient that the binding to cells having the target antigen is detectable compared to the background signal. The diagnostic reagent can be labelled with a radioisotope for camera imaging, or a paramagnetic isotope for magnetic resonance or electron spin resonance imaging.

VII. Other Uses

The antibodies are also useful for affinity purification of selectins and cells expressing the same on their external surfaces. The antibodies can also be used to generate anti-idiotypic antibodies that mimic a selectin domain responsible for antibody binding. Anti-idiotypic antibodies are useful as competitive inhibitors of selectin binding. For example, an anti-idiotypic antibody to a crossreacting P-selectin, E-selectin monoclonal antibody can be selected to compete with P and/or E selectin for binding to their counterreceptors. The antibodies are also useful in screening for a therapeutic agent having the same binding specificity as a crossreacting antibody (see Section I. E).

The following examples are provided to illustrate but not to limit the invention :

EXAMPLE 1

Preparation of Cells Transfected With Selectins

L1-2 murine pre-B cell selectin transfectants are obtained by inserting the respective human selectin genes downstream of the LCMV promoter in pMRB101 or similar plasmid (pMRB101 is a derivative of EEb which contains the *E. coil* gpt gene. Mulligan et al., *Proc. Natl. Acad. Sci. USA* 78: 2072–2076 (1981); Stephans et al., *Nucleic Acids Research* 17: 7110 (1989)). Plasmid DNA is introduced into L1-2 cells by standard methods, such as electroporation, and the cells are selected for resistance to mycophenolic acid. Cells expressing high levels of the appropriate selectin are further selected by "panning" or fluorescence activated cell sorting techniques. See *Lymphocytes, A Practical Approach* (G. C. B. Klaus, IRL Press, Oxford, England, 1987).

EXAMPLE 2

Production of Crossreacting Monoclonal Antibodies

Crossreacting antibodies were produced using two different immunization procedures. In all of these procedures, the inoculum was $10^7$ L1-2 selectin transfectant cells (Berg et al., 1991, 1992, supra) in PBS per injection into mice. In one procedure, Balb/c mice at 4–6 weeks of age (Simonson Labs, Gilroy, Calif.) were injected IP with L1-2$^{E\text{-selectin}}$ transfectants at day 0 and day 14, and L1-2$^{P\text{-selectin}}$ transfectants at day 46, followed by fusion of spleen cells on day 50. In a second procedure, C57/Ld mice at 4–6 weeks of age (Jackson Labs, Bar Harbor, Me.) were immunized in the footpad with hypotonically lysed L1-2$^{E\text{-selectin}}$ cells on day 0, then with intact L1-2$^{E\text{-selectin}}$ cells on days 3 and 6, and with L1-2$^{P\text{-selectin}}$ cells on day 9. The draining lymph node lymphocytes were fused on day 12. In each procedure mouse B-cells were fused with P3X mouse myeloma cells using polyethylene glycol.

Hybridoma supernatants were screened for specify, binding to both E- and P-selectin by two-color FACS analysis. L1-2$^{P\text{-selectin}}$ and L1-2$^{control}$ transfectants were biotinylated by incubation with amino hexanoyl-biotin-N-hydroxy succinimicle (Zymed Labs, South San Francisco, Calif.) at 10 µg/ml in PBS pH 8.0 for 25 min. at RT. After washing, 2×10$^7$ cells/ml were incubated with FITC-Z-Avidin (Zymed Labs, So. San Francisco, Calif.) diluted 1:150 for L1-2$^{P\text{-selectin}}$ cells and 1:1000 for L1-2$^{control}$ cells in FACS Buffer (2% BSA/PBS/10 mM NaN$_3$) for 30 min at 4° C. After washing, cells were mixed with unlabeled L1-2$^{E\text{-selectin}}$ cells at a 1:1:1 ratio in FACS Buffer. 50 µl hybridoma supernatants were added to 200,000 mixed cells in 50 µl in 96-well plates and incubated for 1 hr on ice. After washing, secondary agent was added, 50 µl of 1:500 Goat F (ab')2 anti-mouse IgG-PE conjugated (TAGO, Burlingame, Calif.), for 30 min prior to washing and fixation. FACS analysis was performed on a Becton Dickinson FACScan™ (San Jose, Calif.) according to standard procedures.

Supernatants containing antibodies reacting with both P- and E-selectin were identified by a shift in red fluorescence of the L1-2$^{E\text{-selectin}}$ transfectant (unlabelled with FITC) and the brightest FITC labelled cells (L1-2$^{P\text{-selectin}}$ transfectants). The control L1-2 cells (moderately labelled with FITC) did not show a shift in red fluorescence, indicating that binding was specific for P-selectin and E-selectin. The yield of crossreacting antibodies as a ratio of supernatants screened was 1/844 and 2/57 for the two immunization schedules.

Supernatants showing binding to P and E-selectin transfectants were subcloned by limiting dilution and growl in serum free medium containing residual amounts of FBS. Three E-/P-selectin cross-reacting antibodies, designated 5C7.29; 1D8.10 and 2C9.11, were purified from these supernatants or Protein A-Sepharose (Pierce) according to the recommended protocol. Two antibodies reacting only with E-selectin, 1E4 and 2D4, and an antibody reacting only with P-selectin, 5F4, were identified by the same method. The isotypes of 5C7.29, 1D8.10, 2C9.11, 1E4, and 5F4 were determined to be IgG1, and that of 2D4 was determined to be IgG2a using an Innogenetics Inno-Lia mouse monoclonal antibody isotyping kit (Biosource International, Camarillo, Calif.).

Figure 1B:
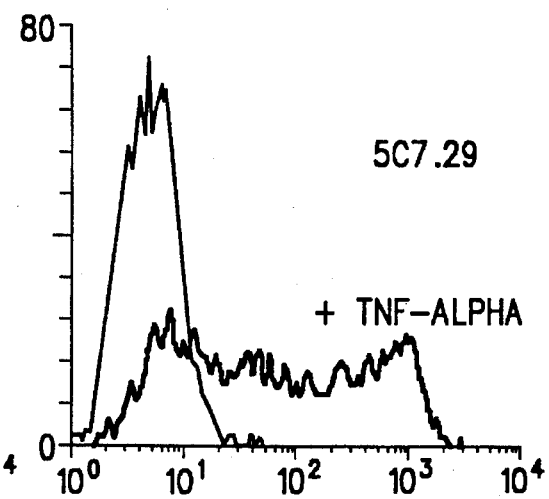

The three E-/P-selectin crossreacting antibodies were also tested for their ability to bind to the natural ligands, rather than the recombinant forms used in the initial screening assays, by single color FACS analysis. The source of natural E-selectin used in these tests was TNF-α-activated human umbilical vein endothelial cells (HUVEC). In activated form, HUVEC cells express E-selectin, but do not express appreciable amounts of P-selectin. FIG. 1b shows that the E-/P-cross-reactive antibody 5C7.29 reacts with TNF-α activated HUVEC (shown by black histograms) but not unactivated HUVEC (grey histograms). Similar results were obtained for the two other cross-reacting antibodies 2C9.11 and 1D8.10. The activated cells also reacted with the anti-E-selectin blocking antibody H18/7 (FIG. 1a) (Becton Dickinson (San Jose, Calif.)), but not with P-selectin-specific antibodies WAPS 12.2 and 5F4. (WAPS 12.2, a P-selectin blocking antibody, was provided by R. Aaron Warnock and Eugene C. Butcher (Stanford, Calif.).)

Figure 2A:
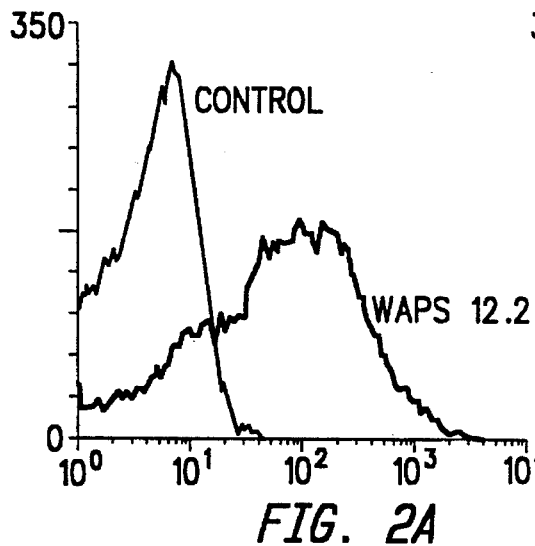
FIGS. 2*a* and 2*b* Crossreacting antibody 5C7.29 binds to naturally occurring P-selectin. (a) Binding of known anti-P-selectin antibody WAPS 12.2 to platelets detected by staining with secondary antibody (black histogram), compared with staining with secondary antibody alone (control, grey histogram). (b) Binding of 5C7.29 to platelets, shown similarly.
Figure 2B:
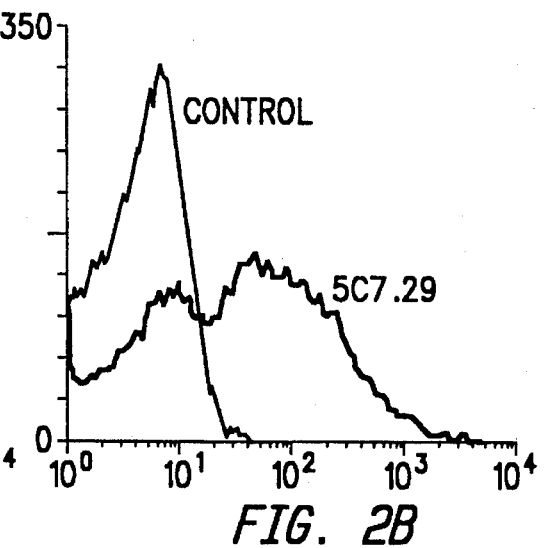

The source of natural P-selectin used in these tests was thrombin-activated platelets. FIG. 2b shows that 5C7.29 binds to these cells as does the known P-selectin antibody WAPS 12.2 (FIG. 2a). Similar results were obtained with 2C9.11 and 1D8.10. Platelets did not significantly react with anti-E-selectin antibodies H18/7 or 1E4.

The E-/P-selectin crossreacting antibodies were further analyzed for binding to L1-2$^{L\text{-selectin}}$ transfectant and with normal human lymphocytes. Specific binding was not observed, demonstrating that the antibodies are specific for E- and P-selectin s and do not bind to L-selectin.

To confirm that the crossreacting antibodies were truly monoclonal, preclearing experiments were performed 10 ng antibody (a limiting amount) was incubated with a large number (10$^7$) of L1-2$^{E\text{-selectin}}$ cells or L1-2$^{P\text{-selectin}}$ cells for 1 hr. The supernatant was then transferred to a second aliquot of L1-2$^{E\text{-selectin}}$ cells or L1-2$^{P\text{-selectin}}$ cells (the same cell type as before) and incubated for 1 hr. Supernatant was transferred to a third aliquot of cells of the same type as before for a further 1 hr incubation. Supernatant was then removed and examined for re activity with L1-2$^{E\text{-selectin}}$, L1-2$^{P\text{-selectin}}$ or L1-2 untransfected cells by one-color FACS analysis.

Figure 3A:
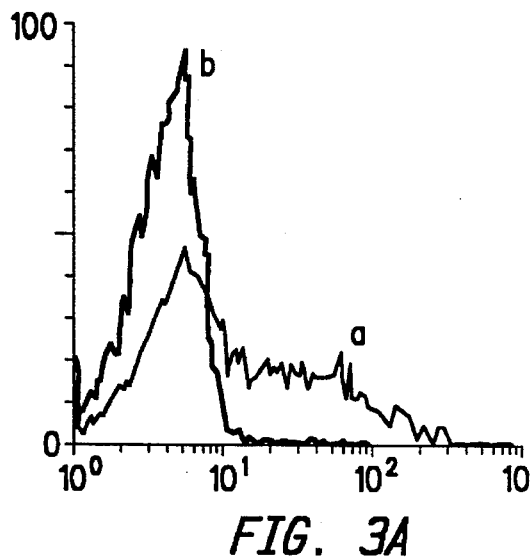
Figure 3B:
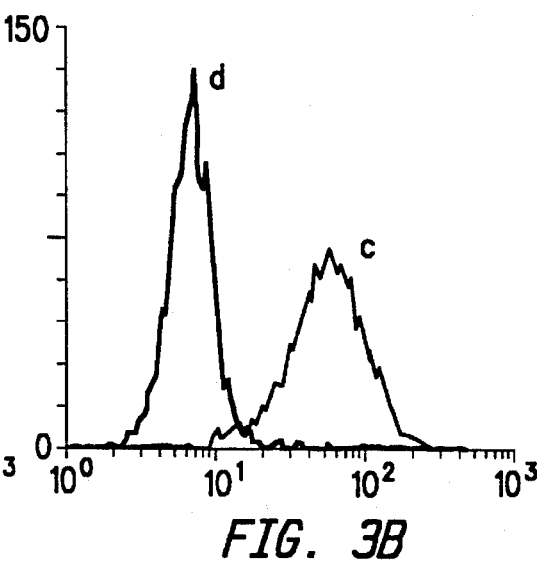

FIGS. 3a and 3b show that preincubation of a solution of the 5C7.29 antibody with L1-2$^{P\text{-selectin}}$ transfectants eliminated subsequent reactivity for both P-selectin and E-selectin Similar results were found following preincubation with L1-2$^{E\text{-selectin}}$ transfectants. These results would be obtained only if the antibody bound to both selectins, and not if the antibody were a mixture of two different antibodies, one reactive with E-selectin and one reactive with P-selectin Therefore, the dual specificities of 5C7.29 reside in the same antibody. Similar results were obtained for the 2C9.11 and 1D8.10 antibodies.

EXAMPLE 3

Inhibition of E-Selectin-Mediated Functions

The antibody 5C7.29 was tested for the ability to block E-selectin mediated functions. In one assay, the antibody was tested for inhibition of HL-60 binding to tumor necrosis factor-α (TNF-α) activated human umbilical vein endothelial cells (HUVEC). This binding assay simulates the binding of neutrophils to endothelial cells in an inflammatory response. The HL-60 cells are a promyelocytic cell line derived from a patient with acute promyelocytic leukemia Collins et al., Nature 270, 347–349 (1977). The HUVEC cells are endothelial cells that when activated with TNF-α for 4–6 hours express E-selectin, and not P-selectin.

HUVEC were obtained from Clonetics (San Diego, Calif.) and cultured as suggested. Confluent cultures, up to passage 6, grown in 8 well plastic Lab Tek slides (Nunc, Naperville, Ill.) were activated for 4 hours with 1 ng/ml TNF-α (R&D Systems, Minneapolis, Minn.). HUVEC cultures were washed and incubated in 0.15 ml Assay Buffer (10% normal bovine serum/10% normal rabbit serum/10 mM HEPES, pH 7.2/RPMI) containing antibodies at 17 µg/ml (i.e., in excess) for 20 min.

HL-60 cells were fluorescently labelled with 6-carboxy-fluorescein diacetate acetoxy-methyl ester (CFDA-AM Molecular Probes, Eugene, Oreg.) (von Andrian et al., 1991, supra) by a 30 min incubation in 10 mg/ml RPMI/10 mM HEPES, pH 7.2, washed and resuspended in Assay Buffer and incubated at RT for 20 min. The resuspended cells ($6 \times 10^5$ cells in 0.15 ml were then added to the HUVEC cultures.

Slides were rotated at 50 rpm on a rotator (Innova 200, New Brunswick Inc.) for 15 min at RT. The cover slips were removed and non-adherent HL-60 cells washed off by dipping slides in DMEM. Adherent cells were fixed by immersion in 1% paraformaldehyde-PBS. Slides were examined microscopically and the number of bound cells per field determined. Two treatments per slide (in quadruplicate) were analyzed.

Figure 4:
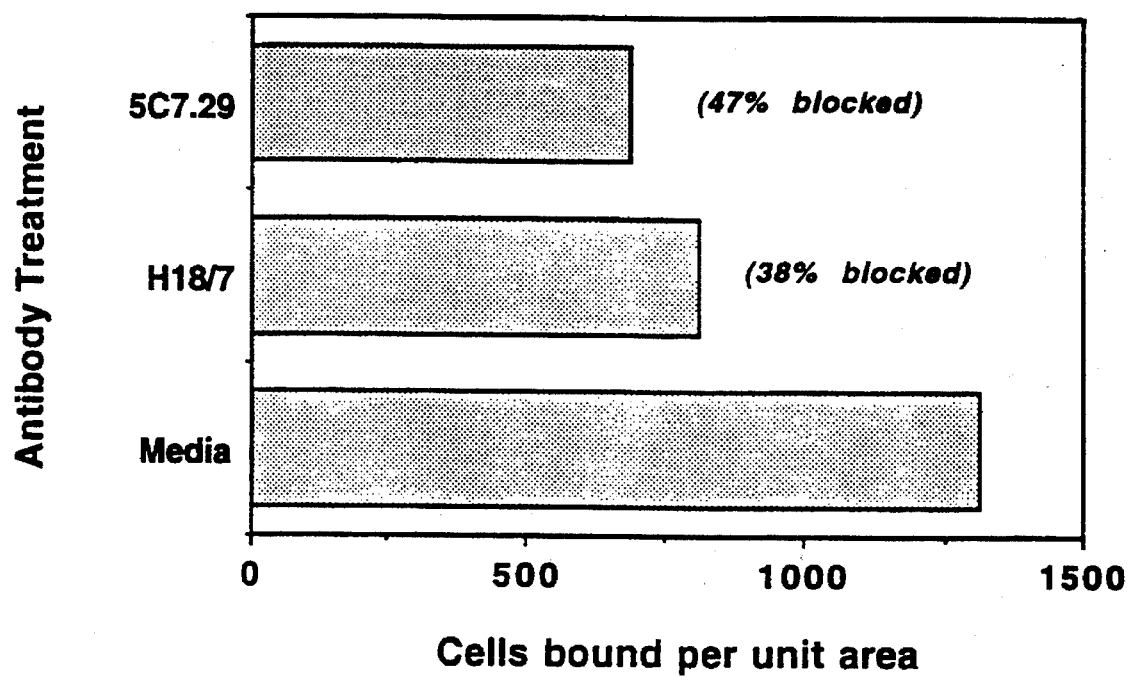

FIG. 4 shows that the number of HL-60 cells binding to the activated HUVEC was decreased 47% by preincubation with 5C7.29. This compared favorably with blocking by the anti-E-selectin-specific antibody H18/7 (38%). Binding was not significantly reduced by a control antibody.

Figure 5:
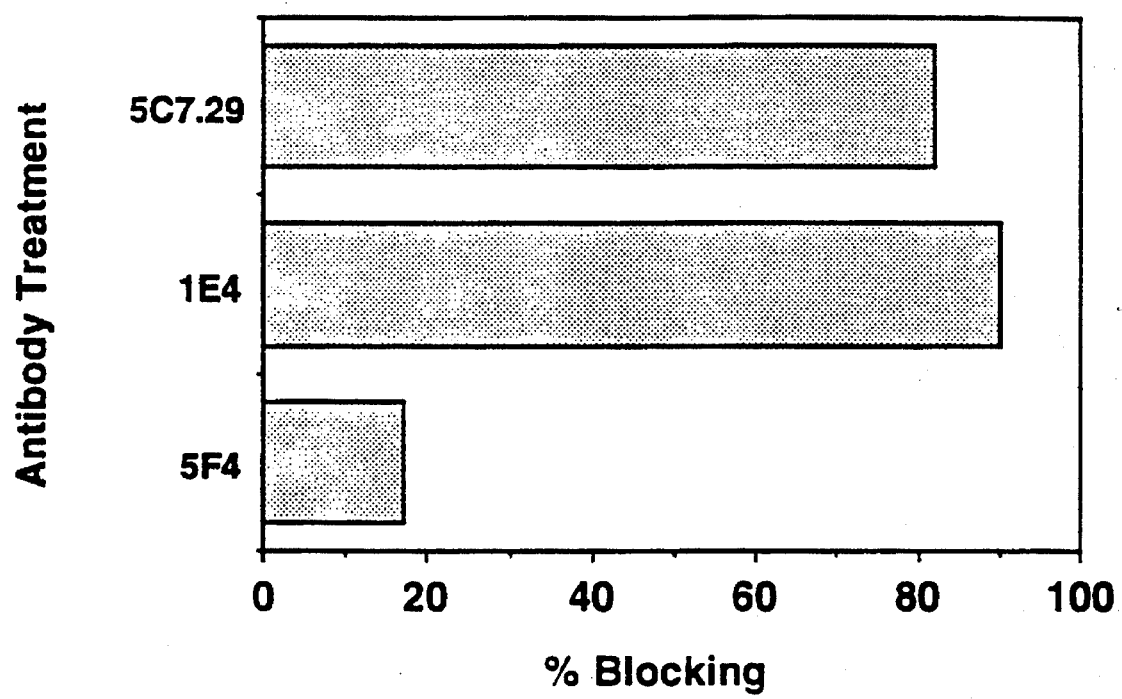
FIG. 5 Monoclonal antibody 5C7.29 blocks binding of HL-60 cells to E-selectin transfectant cells. Average of four experiments.

Because HUVEC can also express P-selectin (although only at low levels under the present activation conditions, 5C7.29 was also tested for HL-60 binding to CHO cells transfected with E-selectin. CHO cells permanently transfected with a truncated form of E-selectin containing the first four N-terminal domains of E-selectin fused to the transmembrane and cytoplasmic domain of another protein were produced according to standard methods. Expression was confirmed by re activity with a control anti- E-selectin antibody (H18/7). Inhibition of binding between fluorescently labelled HL-60 and the transfected CHO cells was performed using the same assay as for the TNF-α-activated HUVEC. 5C7.29 was found to block adhesion by 82% (FIG. 5). Similar results were observed with 1D8.10, 2C9.11 and the E-selectin blocking antibody 1E4. The non-blocking P-selectin specific control antibody 5F4 had no significant effect in this assay.

The cross-reacting antibodies also blocked normal human peripheral blood neutrophil binding to TNF-α-activated HUVEC. At a final concentration of 10 μg/ml, 5C7.29 blocked 71+/−13%, 2C9.11 blocked 62+/−8% and 1D8 blocked 52+/−10% of neutrophil binding to activated HUVEC, while the anti-E-selectin antibodies 1E4 and H18/7 (Bevilacqua et al., 1987, supra) blocked 68+/−4% and 68+/−15%, and a control mouse IgG1 antibody did not block (−21%+/−11%), n=4. For these experiments, neutrophils were isolated from normal human blood by density gradient centrifugation and dextran sedimentation by standard procedures (*Current Protocols in Immunology*, Coligan et al., eds., John Wiley and Sons, New York, 1992) Assays were performed as for HL-60 cells except neutrophils were added to HUVEC at $7.5 \times 10^4$ in 0.15 ml.

EXAMPLE 4

Inhibition of P-selectin-Mediated Functions

Figure 6:
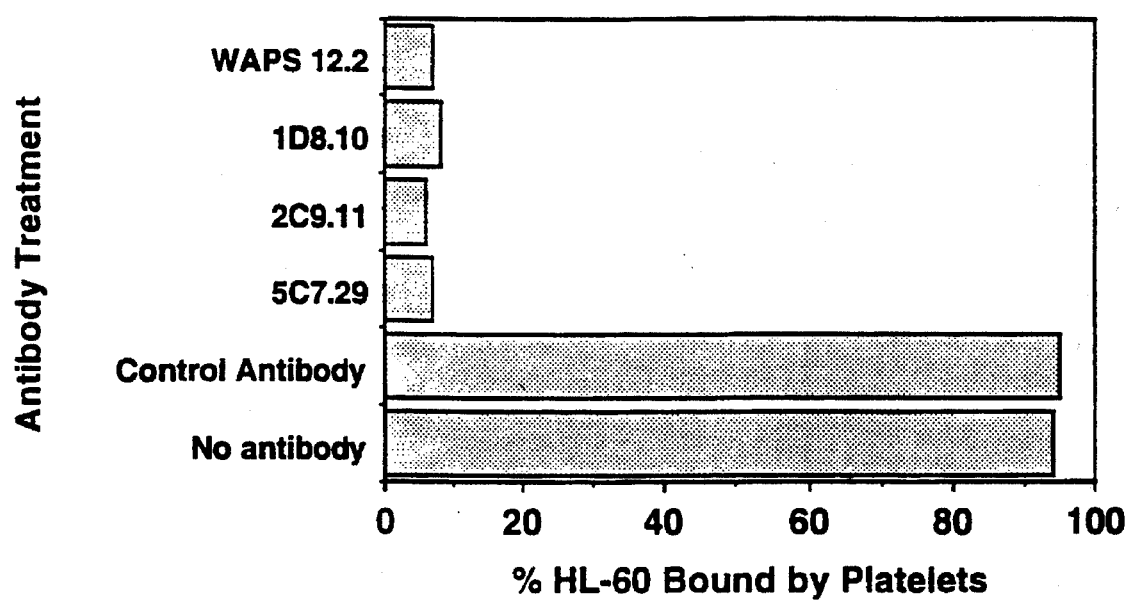
FIG. 6. Monoclonal antibodies 5C7.29, 2C9.11 and 1D8.10 block binding of platelets to HL-60 cells as shown by platelet rosetting. The chart shows the percentage of HL-60 cells with >2 platelets bound (rosetted). Average of three experiments.

The antibodies 5C7.27, 2C7.11 and 1D8.10 were tested for their ability to block P-selectin-mediated functions Blocking was tested in a platelet-HL-60 rosette assay (Corral et al., 1990, supra). The platelets provide a source of cells expressing P-selectin and the HL-60 cells simulate neutrophils. Normal human blood was collected with sodium citrate as anticoagulant and the platelet-rich plasma (PROM prepared by centrifugation at 250 g for 10 min. Platelets were isolated from PRP by centrifugation at 1000 g for 20 min and resuspended at $3 \times 10^8$/ml in PBS, pH 7.2. Monoclonal antibodies (1 μg in 20 μl, i.e., an excess) were added to 20 μl platelets. In some experiments normal human thrombin (0.3 U/μl) was added to activate the platelets as described by Corral et al., 1990, supra. After 45 min. 20 μl HL-60 cells ($10^6$/ml in PBS) were added and further incubated for 45 min. Bound platelets were fixed to HL-60 cells by addition of glutaraldehyde to 1.25%. At least 100 HL-60 cells for each sample were observed microscopically and the number of cells with bound platelets (>2 platelets per HL-60 cell) determined FIG. 6 shows that all three crossreacting antibodies block resetting to about the same extent as the P-selectin specific blocking antibody WAPS 12.2. Similar blocking experiments can be performed using human peripheral blood, neutrophils in place of HL-60 cells. Neutrophils are prepared by the same method and used at the same concentration as described in Example 3.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A humanized monoclonal antibody having a binding site that specifically binds to P-selectin and to E-selectin comprising a humanized heavy chain and a humanized light chain:

(1) the humanized light chain comprising three complementarily determining regions (CDR1, CDR2 and CDR3) having amino acid sequences from the mouse antibody light chain and comprising a variable region framework sequence substantially identical to a human light chain variable region framework sequence; and (2) the humanized heavy chain comprising three complementarily determining regions (CDR1, CDR2 and CDR3 having amino acid sequences from the mouse antibody heavy chain, and comprising a variable region framework sequence substantially identical to a human heavy chain variable region framework sequence;

wherein the humanized antibody specifically binds to the P-selectin with a binding affinity having a lower limit of $10^7$ M$^{-1}$;

wherein the humanized antibody specifically binds to the E-selectin with a binding affinity having a lower limit of $10^7$ M$^{-1}$;

and wherein the specific binding of the antibody to the P-selectin inhibits binding of the P-selectin to a counter-receptor of P-selectin; and the specific binding of the antibody to the E-selectin inhibits binding of the E-selectin to a counter-receptor of E-selectin.

2. The antibody of claim 1 that does not specifically bind to L-selectin.

3. The antibody of claim 2 that is a Fab, Fab', F(ab')$_2$, Fv fragment, or a single-chain antibody.

4. The antibody of claim 2 wherein the complementarily determining regions (CDR1, CDR2 and CDR3 of the light and heavy chains have amino acid sequences from the light and heavy chains of monoclonal antibody 5C7.29, ATCC accession number CRL 11640, respectively.

5. An antibody made by hybridoma 5C7.29, ATCC accession number CRL 11640.

6. A purified nucleic acid segment encoding a light or heavy chain variable region of the antibody of claim 2.

7. A stable cell line comprising:
   a nucleic acid segment encoding the heavy chain of the antibody of claim 2, the segment operably linked to a first promoter to allow expression of the heavy chain;
   a second nucleic acid segment encoding the light chain of the antibody of claim 2, the second segment operably linked to a second promoter to allow expression of the light chain;
   wherein the stable cell line can produce the antibody of claim 2.

8. A pharmaceutical composition comprising a therapeutically effective amount of the monoclonal antibody of claim 2 in an acceptable carrier.

9. A method of treating an inflammatory disease or condition, comprising administering to a human patient a therapeutically effective dose of the pharmaceutical composition of claim 8.

10. The method according to claim 9, wherein the inflammatory disease is ischemia-reperfusion injury.

11. The method of claim 10, wherein the inflammatory disease is ischemia-reperfusion injury after myocardial infarction.

12. A method of generating an antibody capable of blocking E-selectin and P-selectin mediated functions, but not L-selectin mediated functions, the method comprising:
   immunizing a mammal with P-selectin;
   immunizing the mammal with E-selectin;
   immortalizing B-cells from the mammal to obtain immortalized cells producing antibodies; and
   selecting an immortalized cell producing an antibody that specifically binds to E-selectin and to P-selectin, but does not specifically bind to L-selectin, and whose specific binding to P-selectin inhibits binding of P-selectin to a counter-receptor of P-selectin; and whose specific binding of the antibody to E-selectin inhibits binding of E-selectin to a counter-receptor of E-selectin.

* * * * *